United States Patent [19]

Goldenberg

[11] 4,361,544

[45] Nov. 30, 1982

[54] TUMOR LOCALIZATION AND THERAPY WITH LABELED ANTIBODIES SPECIFIC TO INTRACELLULAR TUMOR-ASSOCIATED MARKERS

[76] Inventor: Milton D. Goldenberg, 11837 Gainsborough Rd., Potomac, Md. 20854

[21] Appl. No.: 126,261

[22] Filed: Mar. 3, 1980

[51] Int. Cl.$^3$ ..................... A61K 49/00; A61K 43/00
[52] U.S. Cl. ............................................. 424/1; 424/9
[58] Field of Search ........................................ 424/1, 9

[56] References Cited

U.S. PATENT DOCUMENTS

| | | | |
|---|---|---|---|
| 3,927,193 | 12/1975 | Hansen et al. | 424/1 |
| 3,960,827 | 6/1976 | Björklund | 424/12 |
| 4,144,031 | 3/1979 | Acevedo et al. | 23/230 B |
| 4,146,603 | 3/1979 | Davidson et al. | 424/12 |
| 4,160,019 | 7/1979 | Björklund | 424/12 |
| 4,174,385 | 11/1979 | Reid | 424/12 |

FOREIGN PATENT DOCUMENTS 5638 11/1979 European Pat. Off. ................ 424/1

OTHER PUBLICATIONS

Mach et al., *Europ. J. Cancer*, Suppl. 1, 113, (1978).
Spar, *Sem. Nucl. Med.*, 6, 379, (1976).
Emrich, *Dstch. Med. Wschr.*, 104, 153 (1979).
Lee et al., *Scand. J. Immunol.*, 8 (Suppl. 8), 485 (1978).
Heyderman, *Scand. J. Immunol.*, 8 (Suppl. 8), 119 (1978).
Goldenberg et al., *N. Eng. J. Med.*, 298, 1384 (1978).
Hawthorne et al., *J. Med. Chem.*, 15, 449 (1972).
Order, *Radiology*, 118, 219 (1976).
Ettinger et al., *Cancer Treat. Rep.*, 63, 131 (1979).
Order et al., *Int. J. Radiation Oncology Biol. Phys.*, 6, 703 (1980).
Quinones et al., *J. Nucl. Med.*, 12, 69 (1971).
Hirai et al., *Abstr. 6th Int. Res. Group Carc. Proteins*, Sep. 17–21, 1978, p. 14.
Yoshimoto et al., *Am. J. Obstet. Gynecol.*, 134, 729 (1979).
Begent et al., *J. Royal Soc. Med.*, 73, 624 (1980).
Bale et al., *Cancer Res.*, 40, 2965 (1980).
Gold et al., *Cancer Res.*, 40, 2973 (1980).
Koji et al., *Cancer Res.*, 40, 3013 (1980).
Bagshawe et al., *Cancer Res.*, 40, (1980).
Order et al., *Cancer Res.*, 40, 3001 (1980).
Ghose et al., *Cancer Res.*, 40, 3018 (1980).
Papsidero et al., *Cancer Res.*, 40, 3032 (1980).
McIntire, *Cancer Res.*, 40, 3083 (1980).
Ballou et al., *Science*, 206, 844 (1979).

*Primary Examiner*—Christine M. Nucker
*Attorney, Agent, or Firm*—Millen & White

[57] ABSTRACT

Methods are provided for using radiolabeled antibodies specific to intracellular tumor-associated markers for detection, locatization and therapy of tumors. Antibodies and injectable compositions for use in the methods of the invention are also provided.

26 Claims, No Drawings

TUMOR LOCALIZATION AND THERAPY WITH LABELED ANTIBODIES SPECIFIC TO INTRACELLULAR TUMOR-ASSOCIATED MARKERS

BACKGROUND OF THE INVENTION

U.S. Pat. No. 3,927,193 to Hansen et al discloses a method of tumor localization using labeled antibodies to carcinoembronic antigen (CEA), but provides examples of its use only in animals. Goldenberg et al, *New Eng. J. Med.*, 298, 1384 (1978), reported success in clinical trials of tumor detection and localization by scintillation scanning of patients receiving radiolabeled antibodies to CEA. A special scanner subtraction technique with other radionuclides to compensate for interstitial and blood-pool background activity was considered essential for unequivocal tumor localization using that method.

However, CEA is considered to be primarily a cell-surface antigen, as reported by Heyderman, *Scand. J. Immunol.*, 8. Suppl. 8, 119 (1978), and many others. It had been thought that tumor localization in man using injected radio-labeled tumor-associated antigens required antibodies which were specific to antigens located on the surface of the tumor cell, by Spar, *Seminars In Nucl. Med.*, 6, 379 (1976) and Emrich, *Deutsche Med. Woch.*, 104, 153 (1979). It is known that both human chorionic gonadotropin (HCG) and alpha-fetoprotein (AFP) are cytoplasmic intracellular tumor-associated substances, Heyderman, Supra, Lee et al, Guillouzo et al, Albrechtsen et al and Ruoslahti et al, in *Scand. J. Immunol.*, 8, Suppl. 8, pp. 485ff, 289ff, 165ff and 3ff, respectively (1978). Quinones et al, *J. Nucl. Med.*, 12, 69 (1971) demonstrated that a human choriocarcinoma grown in hamsters could show a 2.8-fold increased uptake of radiolabeled anti-HCG antibody in the tumor as compared to that in the animals' liver. Hirai et al, *Abstracts 6th Int. Res. Group for Carcinoembryonic Proteins*, Marburg/Lahn, Fed. Rep. of Germany, Sept. 17-21, 1978, reported that administration of radiolabeled anti-AFP antibodies to rodents with transplanted human hepatoma, and with rat and human yolk sac tumors, revealed no "homing in" of the antibody in the tumor tissues.

Tumor radiotherapy using labeled antibodies has been suggested by many, and an indication of its success in a single multimodal therapeutic clinical use is reported by Ettinger, Cancer Treat. Rep., 63, 131 (1979). The use of boron-labeled antibodies in therapy is reported by Hawthorne et al., *J. Med. Chem.*, 15, 449 (1972), but the combined incorporation of boron and a radioisotope for localization is not suggested.

A need continues to exist for a method of tumor detection and localization which is not confined to the use of antibodies to cell-surface antigens, which does not require repeated injection of background-compensating material for a subtraction technique, which is adaptable to both diagnosis and therapy, and which has a high reliability and a high resolution.

OBJECTS OF THE INVENTION

Accordingly, it is an object of the present invention to provide a method of tumor localization and detection which achieves high resolution and which uses antibodies to intracellular tumor-associated marker substances.

Another object of the present invention is to provide a method of tumor radiotherapy using antibodies to intracellular tumor-associated marker substances radiolabeled with radiotherapeutically effective radioisotopes.

A further object of this invention is to provide a method of tumor therapy wherein thermal neutrons excite a boron-10 isotope-containing antibody which has been localized by detection of an attached radioisotope label.

Upon further study of the specification and appended claims, further objects and advantages of this invention will become apparent to those skilled in the art.

SUMMARY OF THE INVENTION

The foregoing objects are achieved by providing a method for detecting and localizing a tumor which either produces or is associated with an intracellular marker substance, which comprises injecting a subject parenterally with an antibody specific to said marker substance and radiolabeled with a pharmacologically inert radioisotope capable of detection using a photoscanning device, and subsequently scanning with said device to detect and locate the site or sites of uptake of said labeled antibody by said tumor.

The invention further provides antibodies and injectable compositions for use in the present method, together with methods for tumor therapy using radiolabeled marker-specific tumor-associated antibodies.

DETAILED DISCUSSION

The antibodies used in the present invention are specific to a variety of intracellular tumor-associated antigens as marker substances. These markers may be substances produced by the tumor or may be substances which accumulate within tumor cells, whether in the cytoplasm, the nucleus or in varius organelles or subcellular structures. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. No. 4,150,149 to Wolfsen et al.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies hving higher tumor-specificity, e.g., the beta-subunit of human chorionic gonadotropin (HCG), which stimulates the production of antibodies having a greatly reduced cross-reactivity to non-tumor substances. Suitable such marker substances to which specific antibodies may be raised which are useful in the present invention include, but are not limited to, alpha-fetoprotein (AFP), human chorionic gonadotropin (HCG) and/or its beta-subunit (HCG-beta), colon-specific antigen-p (CSAp), prostatic acid phosphatase, pancreatic oncofetal antigen, placental alkaline phosphatase, pregnancy beta$_1$-globulin, parathormone, calcitonin, tissue polypeptide antigen, T-antigen, beta$_2$-microglobulin, galactyosyl transferase-II (GT-II), gp-52 viral-associated antigen, ovarian cystadenocarcinoma-associated antigen (OCAA), ovarian tumor-specific antigen (OCA), cervical cancer antigens (CA-58, CCA, TA-4), basic fetoprotein (BFP), terminal deoxynucleotidyl transferase (TdT), cystoplasmic melanoma-associated antigens, human astrocytoma-associated antigen (HAAA), common glioma antigen (CGA), glioembryonic antigen (GEA), glial fibrillary acidic protein (GFA), common meningioma antigen (CMA) and tumor angiogenesis factor (TAF).

Marker-specific antibodies may be produced by conventional methods well known in the art. Normally, an animal, preferably a rodent, a rabbit or more preferably a goat or primate is challenged with a tumor-associated marker substance, to which its immune system reacts by producing specific antibodies to these markers. The animal is bled, the immunoglobulin fraction of the blood is isolated, and the specific immunoglobulin isolated by a variety of conventional separation techniques, preferably including one or more affinity chromatography purification steps. Suitable such general methods for raising antibodies specific to tumor-associated marker substances are disclosed inter alia in "Immunodiagnosis of Cancer", Herberman et al, Eds. (Marcel Dekker, Inc., New York and Basel, 1979) and "Cancer Markers", Sell, Ed. (Humana Press, Clifton, N.J. 1980).

Antibodies produced by the foregoing conventional techniques are normally mixtures of antibodies, a certain proportion of which are specific but generally containing a small proportion of antibodies which are cross-reactive with non-tumor-associated antigens. Antibodies purified by repeated affinity chromatography using bound antigens with which some components of the antibody mixture are cross-reactive, as well as passage through a column containing bound purified antigen, have a high specific immunoreactivity, often approaching or even exceeding 70%, and a cross-reactivity with non-tumor associated antigens of less than 15%. These antibodies are considered substantially monospecific to the antigen to which they have been raised, and are preferably used in the present invention.

Highly specific monoclonal antibodies can also be produced by hybridization techniques. Such antibodies normally require little or no purification and normally have a specific immunoreactivity of at least 85%, with specificities of more than 95% in certain cases. Such monoclonal, hybridoma-derived antibodies are also preferred for use in the present invention. In a preferred embodiment, monoclonal antibodies are produced by challenging a monkey with an intracellular tumor-associated marker, fusing antibody-producing monkey lymph or spleen cells with human or mouse myeloma cells to produce hybrid cells which are then isolated, cloned and selected for their ability to produce monoclonal antibodies specific to said marker substance. Monoclonal antibodies from the immunoglobulin G (IgG) fraction are obtained by the present method, and are used to prepare the fragments used for tumor detection, localization and therapy according to this invention. The IgM monoclonal antibodies of Koprowski, U.S. Pat. No. 4,172,124, are unsuitable for use in the present method.

Antibodies may be labeled by any of several techniques known to the art. A wide range of labeling techniques are disclosed in Feteanu "Labeled Antibodies in Biology and Medicine", pages 214–309 (McGraw-Hill Int. Book Co., New York, et al 1978). The introduction of various metal radioisotopes may be accomplished according to the procedures of Wagner et al., *J. Nucl. Med.*, 20, 428 (1979); Sundberg et al., *J. Med. Chem.*, 17, 1304 (1974); and Saha et al, *J. Nucl. Med.*, 6, 542 (1976). The foregoing are merely illustrative of the many methods of radiolabeling proteins known to the art.

Among the radioisotopes used, gamma-emitters, positron-emitters, x-ray-emitters and fluorescence-emitters are suitable for localization and/or therapy, while beta-emitters and alpha-emitters may also be used for therapy. Suitable radioisotopes for labeling antibodies include Iodine-131, Iodine-123, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Tellurium-121m, Tellurium-122m, Tellurium-125m, Thulium-165, Thulium-167, Thulium-168, Technetium-99m and Fluorine-18. The halogens can be used more or less interchangeably as labels since halogen-labeled antibodies and/or normal immunoglobulins would have substantially the same kinetics and distribution and similar metabolism.

A preferred labeling technique involves labeling with either iodine-131 (I-131) or iodine-123 (I-123) using an oxidative procedure wherein a mixture of radioactive potassium or sodium iodide and the antibody is treated with chloramine-T, e.g., as reported by Greenwood et al, *Biochem J.*, 89, 114 (1963) and modified by McConahey et al, *Int. Arch. Allergy Appln. Immunol.*, 29, 185 (1969). This results in direct substitution of iodine atoms for hydrogen atoms on the antibody molecule, presumably on tyrosine residues, possibly also on tryptophane and even on phenylalanine residues, depending on the proportions of reagents and the reaction conditions.

In general, it is desirable to introduce as high a proportion of radiolabel as possible into the antibody molecule without destroying its immunospecificity. While the vast majority of investigators had considered that introduction by direct substitution of more than from 1.5 to 2 iodine atoms per antibody molecule is disadvantageous, it has now been found that the introduction by direct substitution of at least 2.5 and preferably an average of from 5 to 10 iodine atoms per antibody molecule is advantages, especially where the antibody is highly marker-specific prior to labeling. In this case, even a reduction of the antibody specificity of from 5 to 33% as a consequence of high labeling is outweighed by the advantage of high activity, permitting the use of substantially smaller quantities of labeled antibody. As noted above, the use of highly specific antibodies of high activity results in efficient localization and increased resolution. This balancing of increased activity with reduced specificity is advantageous with up to an average of 10 atoms of iodine per antibody molecule after which the reduction in specificity outweighs the advantage of high activity. Using other methods for the introduction of radiolabel, it may be possible to further increase the proportion of label to antibody fragment without paying an unacceptable price in reduced immunospecificity. A further improvement may be achieved by effecting radiolabeling in the presence of the specific antigen, to insure that the antigen binding site on the antibody will be protected. The antigen is separated after labeling.

A further aspect of the present invention relates to the use of antibodies containing both a radioisotope label and an addend containing significant numbers of boron atoms, having at least the 20% natural abundance of boron-10 isotope. The boron-containing addend may be introduced by a variety of methods, preferably by coupling the antibody with a boron-rich coupling agent, such as the diazonium ion derived from 1-(4-aminophenyl)-1,2-dicarbacloso-dodecaborane(12), according to the method of Hawthorne et al, *J. Med. Chem.*, 15, 449 (1972). The boron-10-containing antibody is then radiolabeled according to one or more of the above procedures to produce an antibody containing both one or more radiolabels for tumor localization and/or therapy and a high content of boron-10 atoms for the absorption of thermal neutrons. Boron-10 absorbs thermal neutrons and the activted nucleus decays rapidly to Lithium-7 and an alpha-particle. These resultant alpha-partices are cytotoxic, and their production in tumor cells kills the cells and causes tumor reduction.

Combination of a boron addend with one or more radiolabels on a highly marker-specific antibody provides for the first time a single agent which functions as a multimodal tumor therapeutic agent. The rapid and specific localization of these doubly labeled antibodies at the site of a tumor permits a rapid and precise definition of the areas where neutron irradiation should be focused. Moreover, as tumor cells are destroyed by the combined effects of radiation from the radiolabel and neutron-activated boron-10 emissions, and the killed tumor cells are eliminated, the progress of the radiotherapeutic treatment may be monitored by measurement of the rate of decrease in localized, radiolabeled antibody or other tumor detection method.

Mixtures of labeled antibodies specific to antigens associated with the same or different tumor or tumor cell types may be used. This can enhance detection, localization and/or therapy in certain cases, and can also increase the range of a broad screen for more than one tumor or tumor cell type.

Radioactivity due to accumulation of labeled antibody or its metabolites in the blood-pool or in interstitial fluids can significantly reduce the resolution of tumor localization using labeled antibodies specific to tumor-associated markers. In such cases, it is advantageous to inject a reference substance into the subject prior to photoscanning, the reference substance being radiolabeled with a radioisotope emitting at a different energy from the marker specific antibody label and capable of independent detection by the photoscanning device. The level of activity of the reference substance is used to determine the background activity due to non-targeted specific antibody, this background activity is then subtracted from the total activity of the specific antibody permitting a determination of the activity of substantially only the targeted, tumor-associated antibody. It is known to use technetium-99m-labeled substances for a determination of blood pool and interstitial background activity, as disclosed in Goldenberg et al, *New Eng. J. Med.*, 298, 1348 (1978). That reference discloses the use of Tc-99m-labeled humn serum and Tc-99m-pertechnetate. Separate injection of these reference substances was necessary prior to each photoscan.

The present invention includes the use of Tc-99m-labeled normal immunoglobulin and Tc-99m-labeled sulfur colloid among suitable reference substances. Preferably, however, the reference substance is normal, indifferent immunoglobulin from the same or different species as that used to prepare the specific antibody used as the tumor localization agent. This normal immunoglobulin is preferably radiolabeled with a different isotope of the same element used to label the specific antibody, and is preferably injected concurrently with the radio-labeled marker-specific antibody. This has the advantage of using as a reference substance a molecular species having essentially the same kinetics of binding, distribution and metabolism as the labeled specific antibody. As a consequence, only a single injection of the reference substance is necessary, and increased resolution is achieved.

Suitable such pairs of radioisotopes, one of which may be used for labeling the specific antibody and the other of which is used to label the normal immunoglobulin include Iodine-131 and Iodine-123; Indium-111 and Indium-113m; Gallium-67 and Gallium-68; Ruthenium-97 and Ruthenium-103; or Mercury-197 and Mercury-203. Because iodine may be introduced directly by a chemical substitution reaction, and has at least three isotopes which are radioactive and detectable using a photoscanning device, iodine is preferred for radiolabeling both the specific antibody and the normal immunoglobulin reference substance for use in the method of the invention. Advantageously, Iodine-131 is used for labeling the specific antibody and Iodine-123 is used for labeling the normal immunoglobulin. The resultant emissions are separately detectable on two different channels of a gamma-scintillation detector. The resultant scanning data are conveniently stored in a minicomputer and the aforementioned subtraction procedure is effected to determine the regions of excess accumulation of radiolabeled specific antibody over its ratio to labeled reference immunoglobulin in non-target areas. These values may be used to generate a related output signal, advantageously a gradation of colors on a color television screen. The photoscanning device may also include computed tomographic capabilities. The combination of this highly efficient subtraction technique with the use of highly monospecific, preferably monoclonal antibodies labeled to give the maximum balance between high activity and acceptable immunospecificity provides a tumor localization and detection method of significantly improved resolution.

The antibodies of the invention are advantageously administered in the form of injectable compositions. For general screening, and for many types of localization and therapy, injection will be intravenous, intraarterial or intrathecal. The injectable antibody fragment solution will be administered into a vein, artery or into the spinal fluid over the course of from 2 minutes to about 45 minutes, preferably from 10 minutes to 20 minutes. In certain cases, intradermal or intracavitary administration is advantageous. Where the tumor is supplied by a known artery, intraarterial administration is preferred for therapy. In addition, intrathecal administration may be used for tumors located in the brain. Intradermal and intracavitary administration are advantageous for tumors restricted to areas close to particular regions of the skin and/or to particular body cavities.

A typical injectable composition according to the invention contains about 10 mg human serum albumin (1% USP:Parke-Davis) and from about 20 to 200 micrograms of radiolabeled specific antibody per milliliter of 0.01 M phosphate buffer (pH 7.5: Bioware) containing 0.9% NaCl. Where the subtraction technique of the invention is used, a quantity of radiolabeled normal immunoglobulin roughly equal to the weight of specific antibody is also included. Other conventional pharmaceutically acceptable injection vehicles may be used where indicated, such as for intrathecal, intradermal or intracavitary injection as well as for intravenous or intraarterial injection.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Preparation of $^{131}$I-anti-HCG IgG (goat)

(a) Antibodies to HCG (anti-HCG) are prepared by the method of Bagshawe, in "Methods in Investigative and Diagnostic Endocrinology, Part III, Peptide Hormones", Bearson et al, Eds., pages 756–763 (North-Holland, Amsterdam, 1973).

Antibodies to the β-subunit of HCG (anti-HCG-β IgG) are prepared by the method of Vaitukaitis et al, *Am. J. Obstet. Gynecol.*, 113, 751 (1972).

(b) The antibodies prepared in part (a) are further purified as serum solutions. The procedure is the same for anti-HCG IgG and anti-HCG-β IgG.

The complement of anti-HCG (or anti-HCG-β) serum is inactivated by incubation at 56° C. for one hour, and freed of anti-blood AB human RBC's with a serum/RBC ratio calculated from the hemagglutination assay, until no further hemagglutination activity can be detected. The adsorbed anti-HCG serum is then dialyzed against several volumes of 0.1 M pH/7.0 phosphate buffer (PO$_4$).

(c) A human urinary protein (HUP) immunoadsorbent is prepared by conjugating purified HUP to cyanogen bromide-activated Sepharose 4B (Pharmacia Fine Chemicals, Inc.), using conventional techniques. The conjugation is allowed to proceed overnight at 4° C. with gentle stirring. The HUP-immunoadsorbent is washed with 0.05 M, pH 8.4, borate buffer and resuspended in 4 volumes of 1 M 2-aminoethanol in 0.1 M, pH 8.0 phosphate buffer. The slurry is mixed for one hour at room temperature, filtered and washed with PO$_4$.

An HUP-immunoadsorbent column is prepared, precycled with 2 ml of 10% (v/v) normal goat serum (Gibco), and with approximately one column volume of the chaotropic agent 3 M ammonium thiocyanate, and re-equilibrated with 0.1 M pH 7.0 phosphate buffer.

The HUP-immunoadsorbent column is inserted into an automated chromatographic system and the entire system is thoroughly washed with apyrogenic, sterile PO$_4$. The buffer reservoirs are replaced with reservoirs containing the chaotropic agent and dialyzate.

The adsorbed anti-HCG serum is diluted with PO$_4$ to a volume which is ⅔ that of the void volume of the column and contains an appropriate quantity of antiserum for one cycle through the column. This volume of diluted antiserum is applied and washed into the column with sufficient PO$_4$ to give a total volume of one column void volume. The antiserum is allowed to incubate at room temperature for 20 minutes, then the specific anti-HCG serum, unadsorbed fraction, is eluted from the column with PO$_4$. The column is regenerated by elution with 1.5 to 2 column volumes of 3 M ammonium thiocyanate in PO$_4$ and with 3 to 4 column volumes PO$_4$. The system automatically starts the next cycle by applying a second aliquot of anti-HCG serum. The number of cycles is set to process the entire lot of antiserum.

An aliquot of the anti-HCG serum is concentrated to the original volume of the antiserum and retested by immunodiffusion. The antiserum is tested against reference HCG, an HUP-preparation and normal human tissue extracts and plasma. If the antiserum has a positive reaction against the HUP-preparation, plasma or any normal human tissue extracts, it is recycled with the appropriate immunoabsorbent column.

(d) A HCG-immunoadsorbent column is prepared by conjugating purified HCG to cyanogen bromide-activated Sepharose 4B by a coupling procedure identical to that of the HUP immunoadsorbent, preparing, precycling and equilibrating a column as in part (c).

The HCG-immunoadsorbent column is introduced into the automated chromatographic system and thoroughly washed with apyrogenic PO$_4$. The quantity of anti-HCG serum to be applied with each cycle is calculated on the basis of the radioimmunoassay titration, the sample of antiserum is diluted, applied and incubated as with the HUP immunoadsorbent column. The serum protein including all non-reactive immunoglobulins are eluted from the column with PO$_4$ and are collected as the unadsorbed fraction.

The specific anti-HCG IgG is dissociated and eluted from the column with 3 M ammonium thiocyanate in PO$_4$ and is collected as the adsorbed fraction. In order to remove all traces of the ammonium thiocyanate, the adsorbed fraction is subjected to in-line dialysis by the use of hollow fiber dialysis units (Amicon or BioRad) against 1 M urea and 10% glycerol in PO$_4$. An alternate procedure for dissociation of specific antibody uses guanidine HCl as a chaotropic agent and Sephadex G25 gel filtration chromatography for desalting.

The adsorbed fraction is concentrated at 4° C. by ultrafiltration with PM 30 membranes (Amicon) to a volume facilitating gel filtration chromatography, e.g., a lot of 100 ml of anti-HCG serum is concentrated to approximately 20 ml. The concentrate is dialyzed against 4 changes, 4 hours each, of 100 volumes of 50 mM, pH 7.5, phosphate-buffered slaine (PBS). The anti-HCG IgG preparation is sterile filtered into a sterile, pyrogen-free serum vial. An aliquot is reserved for quality control testing by RIA and immunodiffusion.

(e) A sephacryl S-200 (Pharmacia) column is prepared by washing the gel 5 times with sterile, non-pyrogenic 50 mM, pH 7.5, PBS. The columns are dry-heat sterilized, 180° C. for 3 hours. The column sizes used are 2.6×90 cm or 5.0×90 cm depending on the lot size of the antibody. The prepared column is placed in a refrigerated unit or cold room, equilibrated to 4° C. and thoroughly washed with sterile 50 mM PBS. The column is attached to a U.V. monitor and calibrated with commercial normal goat IgG (Pentex), 50 mg in 20 ml for a 5×90 cm column and 20 mg in 5 ml for the 2.6×90 cm column. It is then washed with three column volumes of PBS.

The lot of goat anti-HCG IgG is applied to the column and eluted with PBS at a flow rate of 6 ml/cm$^2$/hr. The fractions containing IgG protein are pooled and concentrated to approximaely 5 mg IgG protein/ml, $E_{1cm}^{1\%} = 14$ at 280 mμ, dialyzed against PBS, sterile filtered with 0.2 micron Millex units (Millipore) and stored refrigerated in one ml aliquots, approximately 5 mg IgG protein/ml, with sodium azide as a biostatic agent.

(f) Goat anti-HCG IgG, 20 μg IgG per mCi$^{131}$I, is injected into a radionuclide vial containing $^{131}$I (Amersham-Searle).

Chloramine-T and sodium metabisulfite solutions are prepared by the injection of 5 ml of sterile pyrogen-free 0.5 M pH 7.5 phosphate buffer into each of two vials containing 10 mg of chloramine-T and 50 mg of bisulfite, respectively. Chloramine-T solution is injected, 10 μg/mCi$^{131}$I, into the rationuclide vial. Sodium metabisulfite solution, 5 times the amount of chloramine-T, is injected into the vial exactly 90 seconds after the chloramine-T. The mixture is removed from the reaction vial with a sterile syringe, the reaction vial is rinsed twice with 1% normal human serum albumin, and the rinses combined with the reaction mixture.

The sample of $^{131}$I-anti-HCg IgG is applied to a PD-10 Sephadex G-25 column which is pre-equilibrated with 1% normal human serum albumin in PBS, eluted with approximately 4.5 ml of 1% normal human serum albumin in PBS, monitored with a shielded gamma detector (Eberline), collected and diluted to a predetermined concentration for storage and use.

The resultant $^{131}$I-anti-HCG IgG or $^{131}$I-anti-HCG-β IgG has an average of from 3 to 7 atoms of iodine per antibody molecule. Random aliquots from each batch are separately tested for sterility, pyrogenicity, toxicity and other quality control variables.

EXAMPLE 2

(a) Preparation of $^{131}$I-anti-AFP IgG (goat)

Hyperimmune goat antiserum is prepared by repeated intradermal injections of human AFP purified by the procedure of Nishi, Cancer Res., 30, 2507 (1970). The specificity of the antiserum is confirmed by double gel diffusion, immunoelectrophoresis and radioimmunoassay. Immunoelectrophoretically pure IgG is prepared by DEAE-cellulose chromatography of 10 ml antiserum, followed by concentration over an Amicon PM-30 membrane (Amicon, Lexington, Massachusetts). At a concentration of 4.2 mg/ml, the goat anti-AFP IgG had a radioimmunoassay titer of $3 \times 10^5$ using 50 percent binding of a 2 ng labeled antigen as the end point.

The antibody is radiolabeled with I-131 by the procedure of Example 1(f), purified and stored as described in that Example.

(b) Preparation of $^{131}$I-anti-CSAp IgG (goat)

Anti-CSAp serum is prepared by homogenizing GW-39 human colon canceer xenograft tumors in 5 volumes of deionized water (w/v) under ice water by a polytron at full speed for 2 minutes. The homogenate is then centrifuged at $48,000 \times g$ for 1 hour. The clear supernatant is used as immunogen. The protein content of the immunogen is 7 mg/ml as estimated by Lowry's method. A goat is immunized with 5 ml (35 mg protein) of the homogenate emulsified in 5 ml of complete Freund's adjuvant and is given subcutaneously in the neck of the goat. Booster immunizations are continued at 3-4 weeks intervals. The goat is trial bled each month and the serum is tested for antibody production. Bleeding of the 10th month and of later dates are processed by affinity methods for preparation of specific anti-CSAp antibodies.

The anti-CSAp antibodies are affinity purified against vaarious organ and tissue extracts. Tissue extracts of human colon cancer, human spleen and lung and hamster liver and kidney are made in 5 volumes of deionized water (w/v) under ice water by a polytron at full speed for 2 minutes. The homogenates are centrifuged at $48,000 \times g$ for 1 hour. The clear supernatants are collected, lyophilized and redissolved in water to obtain proper protein concentration for conjugation of the antigens to Sepharose 4B by the cyanogen bromide method. Similarly, human and hamster sera are adjusted for protein prior to conjugation to Sepharose 4B. GW-39 water homogenate and its 48,000 g supernatant are treated with 90% liquid phenol for preparation of CSA's, as defined in Goldenberg et al, Cancer Res., 36, 3455 (1976), and conjugated to Sepharose 4B.

Affinity adsorptions were performed according to the procedure of Example 1(c)–(e). Crude goat anti-CSAp (4 ml) is applied to a column containing 100 ml of Sepharose 4B conjugated with colon cancer extract and allowed to flow downwards. The flow is stopped when protein appears in the effluent and then the antiserum is allowed to react for 30 minutes with the immunoadsorbent and then the gel is washed with 0.1 MPO$_4$, pH 7.0 buffer. The adsorbed immunoglobulins are eluted with 3 M NH$_4$SCN in 0.1 m PO$_4$ pH 7.0 buffer. The eluted antibodies are immediately dialysed on Amicon PM-30 membrane and equilibrated with 0.1 M PO$_4$, pH 7.0 buffer followed by 1.0 M urea and 10% glycerol in 0.05 M PO$_4$, pH 7.0, and finally with 0.1 M PO$_4$, pH 7.0 buffer. The antibodies are then passed through a mixture of 75 ml Sepharose 4B conjugated with human spleen, lung and serum. After allowing the antibodies to react with the immunoadsorbent, the column was eluted with 0.1 M PO$_4$, pH 7.0 buffer. The antibodies are concentrated on Amicon PM-30 membrane and passed through a 75 ml of mixture of hamster liver, kidney and serum immunoadsorbent column and processed in the above manner.

Finally, the antibodies are applied to a 320 ml immunoadsorbent column made with phenol extract of GW-39 tumor. After incubating the antibodies for 30 minutes the column is eluted with 0.1 M PO$_4$, pH 7.0 buffer. The antibodies are then concentrated and equilibrated with 0.05 M PO$_4$, pH 7.5 buffer on an Amicon PM-30 membrane. Affinity purified anti-CSAp antibodies obtained thus are applied to a Sephadex G-200 ($2.5 \times 100$ cm) column and fractionated using 0.05 M, pH 7.5 buffer. The IgG fraction is pooled and concentrated on Amicon PM-30. The protein of anti-CSAp IgG is adjusted to 2.8 mg/ml, and stored at $-20°$ C.

The radioiodination of anti-CSAp with I-131 is effected by the procedure of Example 1, and the $^{131}$I-anti-CSAp IgG is purified and stored as in that Example. (c) Using analogous procedures to those of Examples 1 and 2, except for the replacement of HCG, AFP or CSAp by one of prostatic acid phosphatase, pancreatic oncofetal antigen, placental alkaline phosphatase, pregnancy beta$_1$-globulin, parathormone, calcitonin, tissue polypeptide antigen, T-antigen, beta$_2$-microglobulin, galactyosyl transferase-II (GT-II), gp-52 viral-associated antigen, ovarian cystadenocarcinoma-associated antigen (OCAA), ovarian tumor-specific antigen (OCA), cervical cancer antigens (CA-58, CCA, TA-4), basic fetoprotein (BFP), terminal deoxynucleotidyl transferase (TdT), cytoplasmic melanoma-associated antigens, human astrocytoma-associated antigen (HAAA), common glioma antigen (CGA), glioembryonic antigen (GEA), glial fibrillary acidic protein (GFA), common meningioma antigen (CMA) and tumor angiogenesis factor (TAF), and appropriate affinity purification, labeled antibodies to these antigens are obtained.

EXAMPLE 3

Preparation of monoclonal $^{131}$I anti-AFP IgG

Female, 6-month-old, Balb/C mice are injected with 10–100 μg alpha-fetoprotein antigen intraperitoneally, whereby the AFP is mixed in an equal volume (10–100

μl) of incomplete Freund's adjuvant. This is repeated one week later, and again two weeks later, but using the intravenous route without adjuvant. Three-four days later, the mice are killed by cervical dislocation. The optimum time for obtaining antibody against a given antigen varies with the antigen, the route of administration, and the timing of immunization, as well as the interval between the last booster injection and the removal of the spleen cells.

The spleens are removed and placed in 60 mm Petri dishes containing either serum-free medium or Dulbecco's Modified Eagl's Medium (DMEM) with 20% fetal calf serum, at room temperature, and minced with scissors to disperse the cells. The cells are further liberated by agitation for 1-2 min on a Vortex mixer. The spleen cells are removed to a conical centrifuge tube and pelleted at 1,000 rpm in an IEC-MS2 centrifuge, the supernatant is removed, the pellet tapped loose, and then resuspended in 5 ml of cold 0.17 M $NH_4Cl$ for 10 min to lyse red blood cells. Chilled DMEM with 20% fetal calf serum is added and the cells pelleted, and then again suspended in 10 ml DMEM supplemented with 20% fetal calf serum.

The myeloma cell lines used for fusion are maintained in stationary suspension cultures in DMEM with high glucose (4.5 g/L) and 20% fetal calf serum, in 5-10% $CO_2$ at a cell concentration between 100,000 and 1,000,000 per ml. The myeloma (plasmacytoma) cell lines can be P3/X63-Ag8, which is a Balb/C plasmacytoma derived from MOPC-21 (Svasti and Milstein, Biochem. J. 128: 427-444, 1972), or a derivative thereof known as FO (Fazekas de St. Groth and Scheidegger, Basle Institute of Immunology, Basle, Switzerland), or 45.6TG1.7, which is a Balb/C line derived from MPC-11 (Margulies et al., Cell 8: 405-415, 1976). All of these lines lack the enzyme hypoxanthine phosphoribosyl transferase (HPRT; E.C. 2.4.2.8) and are thus killed in a selective medium containing hypoxanthine, aminopterin, and thymidine (HAT), as described by Littlefield (*Science* 145: 709-710, 1964).

The spleen cells obtained from the immunized animal are then fused with the plasmacytoma cells by using polyethylene glycol according to an adaptation of the method of Gelfer et al. (*Somatic Cell Genetic.* 3: 231-236, 1977). For example, a 30% polyethylene glycol solution is made by heating sterile polyethylene glycol 4000 (Merck, molecular weight of about 4,000) (0.5 g Polyethylene glycol+0.05 ml dimethyl sulfoxide (DMSO)+0.5 ml distilled water) and DMEM without serum to 41° C. and mixing 3 ml of polyethylene glycol with 7 ml DMEM without serum, pH 7.4-7.6, and kept at 37° C. until use. Fusions are made at room temperature. The myeloma cells ($10^6$-$10^7$) are washed twice in serum-free medium and then mixed with $1-3\times10^7-1-3\times10^8$ spleen cells in 50 ml conical bottom centrifuge tubes (Falcon 2070). The cells are centrifuged at $250\times g$ for 5 min, and the supernatant fluid is carefully aspirated. An amount of 0.2 ml of the polyethylene glycol preparation is added, and the tube is gently agitated by hand to resuspend the cells. Next, the cells are centrifuged for 3 min at $250\times g$ and again at $400\times g$ for another 3 min, and then kept undisturbed for an additional 3 min. The cells are exposed to polyethylene glycol for about 8 minutes. Thereafter, about 5 ml of serum-free medium is added to the tube, the cells are resuspended gently, and then repelleted by centrifugation at $250\times g$ for 5 min. The supernatant is removed and the cells are suspended in 20 ml of serum-containing medium and incubated at 37° C. in a humidified incubator for 48 hr. before being placed in microplates to which HAT medium is added. Alternatively, the cells are immediately suspended in 30 ml of a medium consisting of DMEM, 10% NCTC 109 medium (Microbiological Associates), 20% fetal calf serum (GIBCO), 0.2 units bovine insulin/ml (Sigma), 0.45 mM pyruvate, 1 mM oxaloacetate, and antibiotics of choice. Thymidine ($1.6\times10^{-5}$ M) and hypoxanthine ($1\times10^{-4}$ M) are added. The cells in this medium are distributed into 6 microplates (Linbro FB 96 TC) with 1 drop (about 50 μl) per well. The next day 1 drop of the above-specified medium containing thymidine and hypoxanthine, now with aminopterin ($8\times10^{-7}$ M), is added to each well. Two drops of the above medium are added 6-7 days later and clones appear microscopically between 10 and 20 days. The hypoxanthine-aminopterin-thymidine (HAT) medium can also be added immediately after the fusion, or at a later time.

An improvement in the number of hybrids obtained is made when a feeder layer is added to each microwell. Here, human fetal fibroblasts are irradiated with 4500 r, and 1,000-2,000 such cells are added to each well, either the day before the fusion or directly to the fused cells and so dispensed with them into the microwells. After clones have appeared macroscopically, the medium is changed by removing most of the medium and adding fresh medium. After a second change of medium, the medium is left there for at least 4 days and then collected for assays of antibody activity and specificity by conventional assays, including radioimmunoassay.

Large amounts of antibody are obtained from spent culture medium harvested from 150 mm plates or roller bottles. The medium is subsequently concentrated by means of a hollow-fiber concentrator (Amicon). Also, antibody is obtained from the ascites fluid of athymic (nude) mice (nu/nu) that were injected 2-3 weeks previously with about 1 billion cloned hybridoma cells. The ascites fluid is diluted with saline by flushing the peritoneal cavity of each mouse with saline, the diluted fluids from each mouse are pooled.

The monoclonal anti-AFP IgG is radiolabeled with I-131 as in Example 1(f).

EXAMPLE 4

Preparation of $^{123}$I-IgG (goat)

Normal goat immunoglobulin G (IgG) (Miles) is affinity purified against cyanogen bromide-linked HCG, AFP and CSAp and labeled with I-123 as in Example 1(f), except that I-123 is substituted for I-131, with proportional changes in the reagents to account for differences in specific activity.

EXAMPLE 5

Preparation of $^{131}$I-anti-AFP-$^{10}$B IgG (a) Anti-AFP IgG prepared according to Example 2(a) is reacted with a 20-fold molar excess of the diazonium salt of 1-(4-aminophenyl)-1,2-dicarba-closo-dodecarborane (12) having a natural abundance of Boron-10 isotope (20%), using the procedure of Hawthorne et al., *J. Med. Chem.*, 15, 449 (1972). The resultant antibody has an average of from 2 to 10 diazo-linked carborane residues or from 4 to 20 Boron-10 atoms per antibody molecule.

(b) The anti-AFP-$^{10}$B of part (a) is radiolabeled with I-131 as in Example 1(f), to introduce an average of from 2.5 to 10 atoms of iodine per antibody molecule.

EXAMPLE 6

Preparation of injectable compositions

Sterile, pyrogen-free solutions are prepared as shown.

(a) A sterile solution containing, per ml:
(1) 10 mg Human Serum Albumin (HSA) (1%, USP, Parke-Davis)
(2) 0.01 M phosphate buffer, pH 7.5 (Bioware)
(3) 0.9% NaCl
(4) 80 μg $^{131}$I-anti-HCG IgG (goat) prepared according to Example 1 (average of about 5 atoms of iodine/molecule, specific activity of about 40 μCi/μg).

The labeled antibody of Example 1 is stored in a solution of (1), (2) and (3) at a concentration of 160 μg/ml and diluted with an equal volume of 1% HSA in phosphate buffered saline (PBS) to prepare this solution.

(b) A sterile solution according to the procedure of part (a) except that it further contains 80 μg/ml of $^{123}$I-IgG as prepared in Example 3. The $^{123}$I-IgG is stored in phosphate buffered saline containing 1% HSA at a concentration of 160 μg/ml. An equal volume of this solution is used in place of 1% HSA in PBS in the procedure of part (a).

(c) A sterile solution according to the procedure of part (b) except that the antibody is the $^{131}$I-anti-AFP IgG (goat) prepared according to Example 2(a), stored in 1% HSA in PBS at a concentration of 160 μg/ml and having comparable activity.

(d) A sterile solution according to the procedure of part (b) except that it further contains 80 μg/ml of $^{133}$I-anti-AFP IgG (monoclonal). The $^{131}$I-anti-HCG IgG, $^{123}$I-IgG and $^{133}$I-anti-AFP IgG are each stored at a concentration of 240 μg/ml and an equal volume of each is used to make the sterile solution.

(e) A sterile solution according to the procedure of part (b) except that the antibody is the $^{131}$I-anti-AFP-$^{10}$B IgG prepared according to Example 5, having an average of 5 diazo-linked carborane groups and an average of 3 iodine atoms per antibody molecule.

EXAMPLE 7

Tumor Localization

Radioiodinated antibody is administered to patients with suspected tumors. The patient is pre-tested for anaphylactic hypersensitivity to goat IgG. To block thyroid uptake of I-131, I-133 or I-123, Lugol's solution (Purepack) is administered by mouth, 5 drops twice daily for seven days beginning one day before injection of the radioactively labeled antibody.

(a) Localization is effected according to the procedure of Goldenberg et al., N.Eng.J. Med., 298, 1384 (1978), by infusion of 0.06 ml of a solution of $^{131}$I-anti-HCG IgG containing $^{123}$I-IgG prepared according to Example 6(b) in 20 ml of sterile physiological saline over a period of from 10 minutes to 20 minutes. No Tc-99m compounds are used, the subtraction technique being adapted in a conventional fashion to discriminate between I-131 and I-123. Scans are taken immediately and at 2, 8, 12, 24, 48 and 72 hours after injection of the antibody is completed.

Data analysis involves storing the photoscanning data in a computer, equalizing the activity level of the labeled normal immunoglobulin with that of the labeled antibody in at least one non-tar area and calculating a background level value for the labeled antibody for each data point; subtracting the resultant background value from the total antibody activity, pixel-by-pixel, to generate a value for the activity of targeted antibody for each data point; and using the resultant generated values for targeted antibody activity to generate a related output signal.

Significant localization is seen after 2 hours, with resolution improving with time, tending to plateau between 8 and 24 hours after injection. No additional background $^{123}$I-IgG is added. The HCG-selectivity of this method is comparable to the CEA-selectivity of the earlier Goldenberg et al method, but the resolution, rapidity and convenience is enhanced significantly.

Imaging is particularly successful in patients with HCG-secreting germ cell tumors of the tests. Secondary pelvic and abdominal tumors in these patients are also successfully located, some of which, e.g., abdominal metastasis, are difficult to impossible to detect by abdominal computerized tomography, intravenous pyelography and inferior venacavography.

(b) The procedure of part (a) is followed, except that the antibody is $^{131}$I-anti-AFP IgG in a solution containing $^{123}$I-IgG as prepared in Example 6(c).

Imaging is comparable to that in part (a), being especially successful in patients with testicular and hepatic cancers. Secondary lung and abdominal metastases are well localized despite serum AFP levels which are often highly elevated.

(c) The procedure of part (a) is followed except that the antibody solution is 0.06 ml of the $^{131}$I-anti-HCG IgG, $^{133}$I-anti-AFP IgG and $^{123}$I-IgG prepared according to Example 6(d). The photoscan data are analyzed by conventional means, separating the I-131, I-133 and I-123 radiation, storing and using the equalized I-123/I-131 and I-123/I-133 ratios to determine the background values for non-targeted antibodies, these being subtracted to compute targeted antibody activities for each antibody separately.

Imaging is successful for all tumor types successfully imaged with the separate antibody scans of parts (a) and (b). The combination scan gives enhanced localization and resolution in many cases, especially embryonal cancers.

EXAMPLE 8

Tumor Therapy (a) A patient having germ-cell cancer of the testis, optionally detected and localized by the procedure of Example 7(a), is injected by intravenous infusion with 150 mCi of the solution of Example 6(a) in 50 ml of sterile physiological saline. Reduction in tumor size is observed within 20 days. The dose is repeated at intervals adjusted on an individual basis.

(b) A patient having a hepatic cancer optionally detected and localized by the procedure of Example 7(b), is injected with an amount of the solution of Example 6(e) (in 50 ml of sterile physiological saline) sufficient to provide 200 μCi of $^{131}$I activity based on a 70 kg patient weight.

The tumor is precisely localized 12 hours after injection using the procedure of Example 6. A well collimated beam of thermal neutrons is focused on the defined tumor locations. Irradiation with an external neutron beam dose of 400–800 rads, delivered in a period of from 8–20 min, is effected for each tumor locus, and is optionally repeated with administration of the tumor-localizing antibody, with or without the radiolabel, at intervals adjusted on an individual basis, but usually not exceeding a total dose of 3200 rads unless simultaneous external neutron beam therapy is indicated.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for detecting and localizing a tumor which either produces or is associated with an intracellular marker substance, which comprises injecting a human subject parenterally with an antibody specific to said marker substance and radiolabeled with a pharmacologically inert radioisotope capable of detection using a photoscanning device, and normal immunoglobulin from the same or different species as that used to prepare said specific antibody, said normal immunoglobulin being radio-labeled with a different isotope of the same element used to label the specific antibody, said different isotope emitting at a different energy from the marker-specific antibody label and being capable of independent detection by said photoscanning device; and subsequently scanning with said device, the level of activity of said normal immunoglobulin being used to determine the background activity due to non-targeted specific antibody, said background activity being subtracted from the total activity of the specific antibody, whereby the activity of substantially only the targeted, tumor-associated antibody is determined, and thereby detecting and localizing the site or sites of uptake of said labeled antibody by said tumor.

2. The method of claim 1, wherein said marker-specific antibody is a substantially monospecific antibody having a marker-specific immunoreactivity prior to labeling of at least 70% and a cross-reactivity to non-tumor-associated antigens of less than 15%.

3. The method of claim 2, wherein said substantially monospecific antibody is a monoclonal antibody.

4. The method of claim 2, wherein said antibody is radiolabeled to an extent sufficient to reduce its marker-specific immunoreactivity by from 5 to 33%.

5. The method of claim 4, wherein said substantially monospecific antibody is radiolabeled with Iodine-131 or Iodine-123, an average of at least 5 atoms of iodine per antibody molecule being introduced by direct substitution of iodine for hydrogen on the antibody molecule.

6. The method of claim 1, wherein said marker substance is an oncofetal antigen.

7. The method of claim 1, wherein said marker substance is a placental antigen.

8. The method of claim 1, wherein said marker substance is an oncogenic or tumor virus associated antigen.

9. The method of claim 1, wherein said marker substance is a tissue- or organ-associated antigen, an ectopic hormone or a normal antigen or variant thereof.

10. The method of claim 1, wherein said marker substance is alpha-fetoprotein (AFP).

11. The method of claim 1, wherein said marker substance is human chorionic gonadotropin (HCG) or its beta-subunit.

12. The method of claim 1, wherein said marker substance is colon-specific antigen-p (CSAp).

13. The method of claim 1, wherein said marker substance is one of prostatic acid phosphatase, pancreatic oncofetal antigen, placental alkaline phosphatase, pregnancy beta$_1$-globulin, parathromone, calcitonin, tissue polypeptide antigen, T-antigen, beta$_2$-microglobulin, transferase-II (GT-II), gp-52 viral-associated antigen, ovarian cystadenocarcinoma-associated antigen (OCAA), ovarian tumor-specific antigen (OCA), cervical cancer antigens (CA-58, CCA, TA-4), basic fetoprotein (BFP), terminal deoxynucleotidyl transferase (TdT), cytoplasmic melanoma-associated antigens, human astrocytoma-associated antigen (HAAA), common glioma antigen (CGA), glioembryonic antigen (GEA), glial fibrillary acidic protein (GFA), common meningioma antigen (CMA) and tumor angiogenesis factor (TAF).

14. The method of claim 1, wherein said radiolabeled normal immunoglobulin is injected concurrently with said radiolabeled marker-specific antibody.

15. The method of claim 1, wherein the specific antibody is labeled with one of a pair of radioisotopes and the normal immunoglobulin is labeled with the other of the pair, said pair being one of Iodine-131 and Iodine-123; Indium-111 and Indium-113m; Gallium-67 and Gallium-68; Ruthenium-97 and Ruthenium-103; or Mercury-197 and Mercury-203.

16. An injectable composition, which comprises
(a) a substantially monospecific antibody having a specific immunoreactivity of at least 70% to an intracellular marker substance produced by or associated with a tumor and a cross-reactivity to non-tumor associated antigens of less than 15%; said antibody being radiolabeled with one of Iodine-131 and Iodine-123 by direct substitution of iodine for hydrogen on the antibody molecule to an extent sufficient to reduce its specific immunoreactivity by from 5 to 33%;
(b) normal immunoglobulin from the same or different species as that used to prepare said specific antibody, said normal immunoglobulin being radiolabeled with the other of Iodine-131 and Iodine-123 by direct substitution of iodine for hydrogen on the immunoglobulin molecule; and
(c) a pharmaceutically acceptable injection vehicle.

17. The composition of claim 16, wherein said monospecific antibody is a monoclonal antibody.

18. The composition of claim 17, wherein said monoclonal antibody is raised in a monkey, and antibody-producing monkey lymph or spleen cells are fused with human or mouse myeloma cells to produce hybrid cells which are isolated, cloned and selected for their ability to produce monoclonal antibodies specific to said marker substance.

19. The composition of claim 16, wherein said marker substance is one of AFP, HCG and CSAp.

20. The composition of claim 16, wherein said marker substance is one of prostatic acid phosphatase, pancreatic oncofetal antigen, placental alkaline phosphatase, pregnancy beta$_1$-globulin, parathormone, calcitonin, tissue polypeptide antigen, T-antigen, beta$_2$-microglobulin, galactyosyl transferase-II (GT-II), gp-52 viral-associated antigen, ovarian cystadenocarcinoma-associated antigen (OCAA), ovarian tumor-specific antigen (OCA), cervical cancer antigens (CA-58, CCA, TA-4), basic fetoprotein (BFP), terminal deoxynucleotic transferase (TdT), cytoplasmic melanoma-associated antigens, human astrocytoma-associated antigen (HAAA), common glioma antigen (CGA), glio-embryonic antigen (GEA), glial fibrillary acidic protein (GFA), common meningioma antigen (CMA) and tumor angiogenesis factor (TAF).

21. An antibody which is specific to an intracellular marker substance produced by or associated with a tumor, said antibody being radiolabeled with a pharmacologically inert radioisotope capable of detection with a photoscanning device, said labeled antibody further containing in chemical combination at least one addend containing at least five atoms of boron with at least a natural abundance of Boron-10 isotope.

22. An injectable composition, which comprises
(a) an antibody which is specific to an intracellular marker substance produced by or associated with a tumor, said antibody being radio-labeled with a pharmacologically inert radioisotope capable of detection with a photoscanning device, said labeled antibody further containing in chemical combination at least one addend containing at least five atoms of boron with at least a natural abundance of Boron-10 isotope; and
(b) a pharmaceutically acceptable injection vehicle.

23. The injectable composition of claim 22, which further comprises normal immunoglobulin from the same or different species as that used to prepare said specific antibody, said normal immunoglobulin being radiolabeled with a different isotope of the same element used to label the specific antibody and emitting at an energy capable of independent detection using said photoscanning device.

24. A method of tumor radiotherapy, which comprises parenterally injecting into a human subject having a tumor which produces or is associated with an intracellular marker substance an effective tumor reducing amount of an antibody which is specific to said marker substance and radiolabeled with a pharmacologically inert, radiotherapeutically effective radioisotope.

25. The method of claim 24, wherein said radioisotope is I-131 and said amount is from 25 to 250 mCi per administration.

26. A method of tumor radiotherapy, which comprises parenterally injecting into a human subject having a tumor which produces or is associated with an intracellular marker substance a radiotherapeutically effective amount of an antibody which is specific to said marker substance and radiolabeled with a pharmacologically inert radioisotope capable of detection with a photo-scanning device, said labeled antibody further containing in chemical combination at least one addend containing at least five atoms of boron with at least a natural abundance of Boron-10 isotope; wherein the location of said tumor is determined using said photoscanning device, and a beam of thermal neutrons is then directed at said tumor location.

* * * * *

UNITED STATES PATENT AND TRADEMARK OFFICE
CERTIFICATE OF CORRECTION

PATENT NO. : 4,361,544
DATED : November 30, 1982
INVENTOR(S) : Milton D. Goldenberg It is certified that error appears in the above-identified patent and that said Letters Patent is hereby corrected as shown below:

Column 16, line 7: reads "polypeptide antigen, T-antigen, beta$_2$-microglobulin,"
should read -- polypeptide antigen, T-antigen, beta$_2$-microglobulin, galactyosyl --

Signed and Sealed this

First Day of March 1983

[SEAL]

Attest:

GERALD J. MOSSINGHOFF

*Attesting Officer*   *Commissioner of Patents and Trademarks*

UNITED STATES PATENT AND TRADEMARK OFFICE
CERTIFICATE OF CORRECTION

PATENT NO. : 4,361,544
DATED : November 30, 1982
INVENTOR(S) : Milton D. Goldenberg It is certified that error appears in the above-identified patent and that said Letters Patent is hereby corrected as shown below:

Column 16, line 7: reads "polypeptide antigen, T-antigen, $beta_2$-microglobulin,"

should read -- polypeptide antigen, T-antigen, $beta_2$-microglobulin galactosyl --

Signed and Sealed this

Twenty-ninth Day of March 1983

[SEAL]

Attest:

GERALD J. MOSSINGHOFF

Attesting Officer

Commissioner of Patents and Trademarks